US007267696B2

(12) United States Patent
Desenne et al.

(10) Patent No.: US 7,267,696 B2
(45) Date of Patent: Sep. 11, 2007

(54) COMPOSITION FOR DYEING KERATINOUS FIBERS, COMPRISING A HYDROXYCARBOXYLIC ACID OR A SALT, READY-TO-USE COMPOSITION COMPRISING IT, IMPLEMENTATION PROCESS AND DEVICE

(75) Inventors: Patricia Desenne, Bois Colombes (FR); Jean-Marie Millequant, Saint-Maur-des-Fosses (FR)

(73) Assignee: L'Oreal S.A. (FR)

( * ) Notice: Subject to any disclaimer, the term of this patent is extended or adjusted under 35 U.S.C. 154(b) by 219 days.

(21) Appl. No.: 10/809,019

(22) Filed: Mar. 25, 2004

(65) Prior Publication Data
US 2004/0221401 A1  Nov. 11, 2004

Related U.S. Application Data

(60) Provisional application No. 60/461,302, filed on Apr. 8, 2003.

(30) Foreign Application Priority Data
Mar. 25, 2003  (FR) .................................. 03 50061

(51) Int. Cl.
*A61K 7/13* (2006.01)
(52) U.S. Cl. ........................ 8/405; 8/406; 8/410; 8/411; 8/421; 8/435; 8/552; 8/554; 8/594
(58) Field of Classification Search .................... 8/405, 8/406, 410, 411, 421, 435, 552, 554, 594
See application file for complete search history.

(56) References Cited

U.S. PATENT DOCUMENTS

| 2,261,002 A | 10/1941 | Ritter ........................... 260/520 |
| 2,271,378 A | 1/1942 | Searle ....................... 260/256.4 |
| 2,273,780 A | 2/1942 | Dittmar ........................ 160/28 |
| 2,375,853 A | 5/1945 | Kirby et al. ................. 260/583 |
| 2,388,614 A | 11/1945 | Kirby et al. .................... 987/22 |
| 2,454,547 A | 11/1948 | Beck et al. ............... 260/567.6 |
| 2,528,378 A | 10/1950 | Mannheimer ............ 260/509.6 |
| 2,781,354 A | 2/1957 | Mannheimer ............ 260/309.6 |
| 2,961,347 A | 11/1960 | Floyd ........................... 117/141 |
| 3,206,462 A | 9/1965 | McCarty et al. ............... 260/28 |
| 3,227,615 A | 1/1966 | Korden ....................... 167/87.1 |
| 3,472,840 A | 10/1969 | Stone et al. ................. 260/231 |
| 3,632,559 A | 1/1972 | Matter et al. .................. 260/78 |
| 3,696,044 A | 10/1972 | Rutledge |
| 3,836,537 A | 9/1974 | Boerwinkle et al. ... 424/248.56 |
| 3,874,870 A | 4/1975 | Green et al. ................. 424/160 |
| 3,915,921 A | 10/1975 | Schlatzer, Jr. .............. 260/24.6 |
| 3,917,817 A | 11/1975 | Vanlerberghe et al. ........ 424/70 |
| 3,929,990 A | 12/1975 | Green et al. ............. 424/248.6 |
| 3,966,904 A | 6/1976 | Green et al. ................... 424/78 |
| 4,001,432 A | 1/1977 | Green et al. ............. 260/256.4 |
| 4,005,193 A | 1/1977 | Green et al. ................. 424/468 |
| 4,025,617 A | 5/1977 | Green et al. ................. 424/329 |
| 4,025,627 A | 5/1977 | Green et al. ................... 424/20 |
| 4,025,653 A | 5/1977 | Green et al. ................. 424/325 |
| 4,026,945 A | 5/1977 | Green et al. ............. 260/567.6 |
| 4,027,020 A | 5/1977 | Green et al. ................... 424/28 |
| 4,031,307 A | 6/1977 | DeMartino et al. ......... 536/141 |
| 4,075,136 A | 2/1978 | Schaper ...................... 260/2 R |
| 4,131,576 A | 12/1978 | Iovine et al. ............... 260/17.4 |
| 4,157,388 A | 6/1979 | Christiansen ............... 260/17.4 |
| 4,349,532 A | 9/1982 | Vanlerberghe et al. ........ 424/47 |
| 4,381,919 A | 5/1983 | Jacquet et al. ................. 81/405 |
| 4,445,521 A | 5/1984 | Grollier et al. ................. 132/7 |
| 4,509,949 A | 4/1985 | Huang et al. ................ 586/158 |
| 4,540,510 A | 9/1985 | Karl ......................... 252/315.3 |
| 4,666,712 A | 5/1987 | Hollenberg et al. ........ 424/70.1 |
| 4,702,906 A | 10/1987 | Jacquet et al. ................ 424/70 |
| 4,719,282 A | 1/1988 | Nadolsky et al. ............ 528/370 |
| 4,996,059 A | 2/1991 | Grollier et al. ................ 424/21 |
| 5,089,252 A | 2/1992 | Grollier et al. .............. 424/147 |
| 5,621,008 A | 4/1997 | Ptchelintsev |
| 5,786,313 A | 7/1998 | Schneider |
| 5,804,172 A | 9/1998 | Ault ........................... 424/70.1 |
| 6,156,296 A * | 12/2000 | Riedel et al. ............... 424/70.1 |
| 6,254,646 B1 | 7/2001 | Di La Mettrie et al. |
| 6,260,556 B1 | 7/2001 | Legrand et al. ............. 132/208 |
| 6,379,401 B1 | 4/2002 | Legrand et al. ................. 8/431 |
| 6,540,791 B1 | 4/2003 | Dias |

(Continued)

FOREIGN PATENT DOCUMENTS

DE          19733841          2/1999

(Continued)

OTHER PUBLICATIONS

Fonnum et al., "Associative thickeners. Part I: Synthesis, rheology and aggregation behavior," Colloid & Polymer Science 271:380-89 (1993).

(Continued)

*Primary Examiner*—Eisa Elhilo
(74) *Attorney, Agent, or Firm*—Lerner, David, Littenberg, Krumholz & Mentlik, LLP

(57) ABSTRACT

The present invention relates to a composition for dyeing keratin fibers, comprising, in a medium that is suitable for dyeing, a) at least one oxidation base and/or at least one direct dye, and b) at least one particular hydroxycarboxylic acid or a salt thereof. The invention also relates to a ready-to-use composition comprising the above-mentioned composition and an oxidizing agent. The invention also relates to a process for dyeing keratin fibers, in which a composition according to the invention and optionally an oxidizing composition, these compositions being mixed extemporaneously before use or applied successively, are applied to the said fibers; the composition(s) is(are) left on the fibers for a time that is sufficient to obtain the desired coloration; the fibers are rinsed to remove therefrom the composition according to the invention and optionally the oxidizing composition; the fibers are optionally washed, they are rinsed after each washing, and are optionally dried. Finally, the invention relates to a device for implementing the process.

61 Claims, No Drawings

U.S. PATENT DOCUMENTS

| | | |
|---|---|---|
| 2001/0008031 A1 | 7/2001 | Cannell et al. |
| 2001/0023515 A1* | 9/2001 | Cottard et al. .................. 8/406 |
| 2002/0127194 A1 | 9/2002 | Devin-Baudoin |
| 2003/0032573 A1 | 2/2003 | Kinderdine |
| 2004/0001792 A1 | 1/2004 | Biatry .......................... 424/67 |
| 2004/0074015 A1 | 4/2004 | Kravtchenko et al. ......... 8/406 |
| 2005/0011017 A1 | 1/2005 | Legrand et al. |
| 2005/0129644 A1 | 6/2005 | Sabbagh et al. |

FOREIGN PATENT DOCUMENTS

| | | |
|---|---|---|
| DE | 10109730 | 9/2002 |
| EP | 0122324 | 10/1984 |
| EP | 0216479 | 4/1987 |
| EP | 0 237 111 | 9/1987 |
| EP | 0337354 | 10/1989 |
| EP | 0375388 | 6/1990 |
| EP | 0488242 | 6/1992 |
| EP | 0 509 382 A2 | 10/1992 |
| EP | 0531111 | 3/1993 |
| EP | 2818545 | 12/2000 |
| EP | 1 374 849 | 1/2004 |
| EP | 1374849 | 1/2004 |
| FR | 2100198 | 3/1972 |
| FR | 2633940 | 1/1990 |
| FR | 2818545 | 12/2000 |
| FR | 2814943 | 4/2002 |
| GB | 1021400 | 3/1966 |
| GB | 1347051 | 2/1974 |
| GB | 1494915 | 12/1977 |
| GB | 1510489 | 5/1978 |
| GB | 1513672 | 6/1978 |
| GB | 1546809 | 5/1979 |
| GB | 1604473 | 12/1981 |
| GB | 2193501 | 2/1988 |
| JP | 62-132814 | 6/1987 |
| JP | 2003/081782 | 6/1987 |
| JP | 11 343217 | 3/2000 |
| WO | WO-94/04125 | 3/1994 |
| WO | WO-01/62221 | 8/2001 |
| WO | WO-01/97755 | 12/2001 |
| WO | WO-02/16538 | 2/2002 |
| WO | WO-02/067875 | 2/2002 |
| WO | WO-02-064151 A1 | 8/2002 |
| WO | WO-03/015725 | 8/2002 |
| WO | WO-03/015730 | 2/2003 |
| WO | WO-03/015732 A1 | 2/2003 |

OTHER PUBLICATIONS

Kojima et al., "Hair preparations containing reducing agents, metallic salts, dyes, and oxidizing agents," Chemical Abstracts JP 62 132814.

Kojima, et al., "Hair preparations containing reducing agents, metallic salts, dyes, and oxidizing agents," Chemical Abstracts JP 62 132814, Jun. 16, 1987.

STIC Search Report dated Nov. 9, 2006 for U.S. Appl. No. 10/809,564.

* cited by examiner

COMPOSITION FOR DYEING KERATINOUS FIBERS, COMPRISING A HYDROXYCARBOXYLIC ACID OR A SALT, READY-TO-USE COMPOSITION COMPRISING IT, IMPLEMENTATION PROCESS AND DEVICE

CROSS-REFERENCE TO RELATED APPLICATIONS

The present invention claims the benefit of French Provisional Application No. 0350061, filed Mar. 25, 2003, and U.S. Provisional Application No. 60/461,302, filed Apr. 8, 2003, the disclosures of which are incorporated by reference herein.

The present invention relates to a composition for dyeing a keratinous fiber, comprising a) at least one oxidation base or direct dye or a mixture thereof, and b) at least one particular hydroxycarboxylic acid or a salt thereof. The invention also relates to a ready-to-use composition comprising the dye composition, and to an implementation process and a device.

BACKGROUND OF THE INVENTION

It is known practice to use dye compositions containing oxidation dye precursors, which are generally known as oxidation bases, direct dyes or combinations thereof to dye keratinous fibers, more preferably human keratinous fibers, such as hair. Oxidation bases are colorless or weakly colored precursors, which, when combined with oxidizing products, can give rise to colored compounds and dyes via a process of oxidative condensation. The shades obtained with these oxidation bases may be varied by combining them with couplers or coloration modifiers. Direct dyes are, themselves, colored molecules and dyes with affinity for fibers. When direct dyes are applied in the presence of an oxidizing agent, this is referred to as lightening dyeing.

Usually, dye compositions comprise at least one sequestering agent chosen from ethylenediaminetetraacetic acid (EDTA) and derivatives thereof, for instance diethylenetriaminepentaacetic acid (DPTA). The role of these agents is to complex the metal cations liable to be present in trace amounts in the compositions, and also those that may be present on the hair and originating from the ambient air, from the water with which the hair has been washed, or from shampoos or other hair products with which the hair has been treated. Specifically, it is very important to neutralize these metal cations, since they are liable to catalyze oxidation reactions on the hair fibers, in an uncontrolled manner, which may be reflected by severe adverse effects such as embrittlement of the hair or burning of the scalp.

Dye compositions comprising such sequestering agents give good coloration properties, but may, however, be further improved.

SUMMARY OF THE INVENTION

Thus, one preferred embodiment of the present invention is a composition for dyeing a keratinous fiber, comprising:
a) at least one oxidation base or direct dye or a mixture thereof;
b) at least one compound of formula (I):

wherein R represents a $CH_2OH$ or $CO_2X$ group, and X represents a hydrogen atom or a monovalent or divalent cation chosen from an alkali metal, alkaline-earth metal, transition metal, organic amine or ammonium ion; and
c) a suitable medium,
wherein when R is a $CH_2OH$ group, the compound of formula (I) is not gluconic acid or its salt.

Specifically, gluconic acid includes its alkali metal salt, alkaline-earth metal salt, transition metal salt, an organic amine salt, and an ammonium salt or a mixture thereof.

Another preferred embodiment of the invention is a ready-to-use composition comprising the above-mentioned composition and at least one oxidizing agent.

Yet another preferred embodiment of the invention consists of a process for bleaching a keratin fiber, successively comprising the following steps:
a) mixing a composition comprising, at least one oxidation base or direct dye or a mixture thereof, at least one above-mentioned compound of formula (I), a suitable medium and optionally an oxidizing composition, are applied to the keratin fibers;
b) applying the mixed composition contemporaneously;
c) leaving the composition on the fibers for a time that is sufficient to obtain the desired coloration;
d) rinsing the keratinous fibers to remove therefrom the composition according to the invention and optionally the oxidizing composition;
e) optionally washing and rinsing the keratin fibers; and
f) optionally drying the fibers.

Finally, another preferred embodiment of the invention is a device for dyeing keratin fibers, comprising at least two compartments wherein, one of the at least two compartments comprising a composition according to the invention, the other at least two compartments comprising an oxidizing composition comprises at least one oxidizing agent in a medium that is suitable for dyeing.

Specifically, it has been found that the presence of compound(s) corresponding to those of formula (I) and used as sequestering agents in dye compositions makes it possible to improve the rise of the dye in the hair and/or to reduce the coloration difference (reduce the selectivity) between the differently sensitised hair or portions of hair. It is recalled that hair is sensitised when it has undergone dyeing, bleaching or permanent-reshaping treatments.

Moreover, the shades obtained show good fastness with respect to external attack (shampooing, light, permanent-waving, etc.).

In addition, the compound of formula (I) used as complexing agent in the dye composition according to the invention has the advantage of being totally harmless to the skin and especially of being free of any allergenic nature.

Moreover, it shows good biodegradability and its production cost or purchase cost allows it to be used in compositions intended to be sold not only to professionals, but also in mass distribution (especially supermarkets and hypermarkets).

As indicated previously, the composition according to the invention comprises, in a medium that is suitable for dyeing, at least one oxidation base delete or delete direct dye or a mixture thereof.

DETAILED DESCRIPTION OF THE INVENTION

Oxidation Bases

The oxidation base may be chosen from the oxidation bases conventionally used for oxidation dyeing, for instance para-phenylenediamines, bis(phenyl)alkylenediamines, para-aminophenols, ortho-aminophenols and heterocyclic bases, and the addition salts thereof with an acid or with an alkaline agent, alone or as mixtures.

Among the para-phenylenediamines that may be mentioned, more preferably are, for example, para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylene-diamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)-amino-2-methyl-aniline, 4-N,N-bis(β-hydroxyethyl)-amino-2-chloroaniline, 2-β-hydroxyethyl-para-phenylene-diamine, 2-fluoro-para-phenylene-diamine, 2-isopropyl-para-phenylene-diamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylamino-ethyloxy-para-phenylenediamine, N-(β-methoxyethyl)-para-phenylenediamine and 4'-aminophenyl-1-(3-hydroxy) pyrrolidine, and the addition salts thereof with an acid or with an alkaline agent.

Among the bis(phenyl)alkylenediamines that may be mentioned more preferably, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylamino-phenyl)tetramethylenediamine, N,N'-bis(ethyl)-N,N'-bis(4'-amino-3'-methylphenyl)ethylenediamine and 1,8-bis(2,5-diamino-phenoxy)-3,5-dioxaoctane, and the addition salts thereof with an acid or with an alkaline agent.

Among the para-aminophenols that may be mentioned more preferably, for example, are para-aminophenol, 4-amino-3-methylphenol, 4-amino-3-fluorophenol, 4-amino-3-hydroxy-methylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylamino-methyl)phenol and 4-amino-2-fluorophenol, and the addition salts thereof with an acid or with an alkaline agent.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be mentioned especially are pyridine derivatives, pyrimidine derivatives and pyrazole derivatives, and the addition salts thereof with an acid or with an alkaline agent.

Usually, when the composition comprises one or more oxidation bases, the content of these compounds ranges between 0.0005% and 12% by weight relative to the total weight of the composition and preferably from 0.005% to 6% by weight relative to the same reference.

Coupler

If it is desired to vary the shades obtained with these oxidation bases, it is often preferred to combine them with at least one coupler.

The couplers may be chosen especially from meta-phenylenediamines, meta-aminophenols, meta-diphenols and heterocyclic couplers, and the addition salts thereof with an acid or with an alkaline agent.

The couplers that are more particularly preferred are those chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxy-ethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo [1,5-b]-1,2,4-triazole, 2,6-dimethyl [3,2-c]-1,2,4-triazole and 6-methylpyrazolo [1,5-a] benzimidazole, and the addition salts thereof with an acid or with an alkaline agent.

When they are present, the coupler(s) represent(s), for example, from 0.0001% to 10% by weight relative to the total weight of the composition and preferably from 0.005% to 5% by weight relative to the same reference.

In general, the addition salts with an acid that may be used in the context of the compositions of the invention are chosen especially from the hydrochlorides, hydrobromides, sulphates, citrates, succinates, tartrates, tosylates, benzene-sulphonates, lactates and acetates.

The addition salts with an alkaline agent that may be used in the context of the invention are chosen especially from the addition salts with alkali metals or alkaline-earth metals, with ammonia and with organic amines, including alkanolamines and the compounds having the following formula:

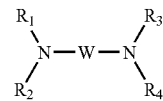

in which W is a propylene residue optionally substituted with a hydroxyl group or a $C_1$-$C_6$ alkyl radical; $R_1$, $R_2$, $R_3$ and $R_4$, which may be identical or different, represent a hydrogen atom or a $C_1$-$C_6$ alkyl radical optionally bearing at least one hydroxyl radical.

Direct Dyes

The composition according to the invention may comprise, in place of or in combination with the oxidation base(s) optionally combined with one or more couplers, at least one direct dye.

The direct dyes are more preferably compounds that absorb light radiation in the visible range (400-750 nm).

They may be of nonionic, anionic or cationic nature.

In general, these direct dyes are chosen from nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes and dyes derived from triarylmethane, alone or as mixtures.

Among the nitrobenzene dyes that may be mentioned are the following red or orange compounds: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxy-ethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine and 1-amino-2-nitro-4-hydroxy-5-methylbenzene, alone or as mixtures.

As regards the nitrobenzene direct dyes, yellow and green-yellow dyes of this type may be used, for instance 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-di(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulphonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl)amino-3-nitrobenzamide.

It may even be envisaged to use blue or violet nitrobenzene dyes, for instance, inter alia, 1-(β-hydroxyethyl)amino-4-N,N-bis(β-hydroxyethyl)amino-2-nitrobenzene, 1-(γ-hydroxypropyl)amino-4,N,N-bis-(β-hydroxyethyl)amino-2-nitrobenzene, 1-(β-hydroxyethyl)amino-4-(N-methyl-N-β-hydroxyethyl)amino-2-nitrobenzene, 1-(β-hydroxyethyl)amino-4-(N-ethyl-N-β-hydroxyethyl)amino-2-nitrobenzene, 1-(β,γ-dihydroxypropyl)amino-4-(N-ethyl-N-β-hydroxyethyl)amino-2-nitrobenzene, 2-nitroparaphenylenediamines having the following formula:

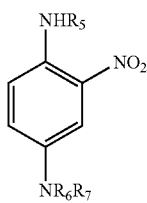

in which:
R₆ represents a $C_1$-$C_4$ alkyl radical or a β-hydroxy-ethyl, β-hydroxypropyl or γ-hydroxypropyl radical;
R₅ and R₇, which may be identical or different, represent a β-hydroxyethyl, β-hydroxypropyl, γ-hydroxypropyl or β,γ-dihydroxypropyl radical, at least one of the radicals R₆, R₇ or R₅ representing a γ-hydroxypropyl radical and R₆ and R₇ not simultaneously being able to denote a β-hydroxyethyl radical when R₆ is a γ-hydroxypropyl radical, such as those described in French patent FR 2 692 572.

It is recalled that azo dyes are compounds comprising in their structure at least one —N=N— sequence not included in a ring; methine dyes are compounds comprising in their structure at least one —C=C— sequence not included in a ring; azomethine dyes are compounds comprising in their structure at least one —C=N— sequence not included in a ring.

The dyes derived from triarylmethane comprise in their structure at least one sequence below:

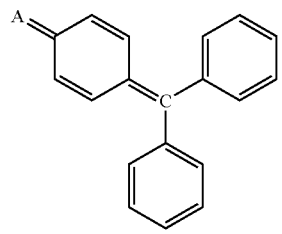

A denoting an oxygen or nitrogen atom.

The xanthene dyes comprise in their structure at least one sequence of formula:

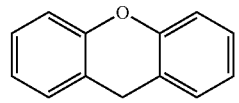

The phenanthridine dyes comprise in their structure at least one sequence of formula:

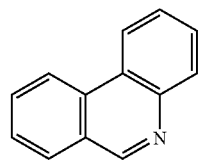

The phthalocyanine dyes comprise in their structure at least one sequence of formula:

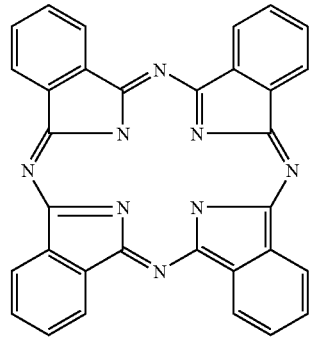

The phenothiazine dyes comprise in their structure at least one sequence below:

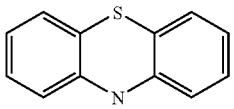

The direct dyes may moreover be chosen from basic dyes such as those listed in the Color Index, 3rd edition, preferably under the names "Basic Brown 16", "Basic Brown 17", "Basic Yellow 57", "Basic Red 76", "Basic Violet 10", "Basic Blue 26" and "Basic Blue 99"; or from the acidic direct dyes listed in the Color Index, 3rd edition, under the names "Acid Orange 7", "Acid Orange 24", "Acid Yellow 36", "Acid Red 33", "Acid Red 184", "Acid Black 2", "Acid Violet 43", and "Acid Blue 62", or alternatively cationic direct dyes such as those described in patent applications WO 95/01772, WO 95/15144 and EP 714954, the content of which forms an integral part of the present invention.

When they are present, the direct dye(s) preferably represent(s) from 0.0005% to 12% by weight approximately relative to the total weight of the composition, and even more preferably from 0.005% to 6% by weight approximately relative to this weight.

Complexing Compound

The composition also comprises at least one compound of formula (I):

R—(CHOH)$_4$—CO$_2$X  (I)

wherein R represents a CH$_2$OH or CO$_2$X, group and X represents a hydrogen atom or a monovalent or divalent cation chosen from an alkali metals, alkaline-earth metal, transition metal, organic amine or ammonium ion, wherein when R represents a CH$_2$OH group, the compound of formula (I) is not gluconic acid.

Since formula (I) comprises 4 chiral groups of H—C—OH atoms, and even 5 when R represents a CH$_2$OH group, it is known to the skilled in the art that this formula includes enantiomers, diastereoisomers, racemic mixtures and other mixtures that may correspond to this formula.

As examples of alkali metal cations, mention may be made preferably of sodium (Na$^+$) and potassium (K$^+$), and as examples of alkaline-earth metal cations, mention may be made preferably of calcium (Ca$^{2+}$) and magnesium (Mg$^{2+}$).

For the purposes of the present invention, the term "transition metal" means a metal comprising an incomplete d sub-shell, more preferably in oxidation state II, such as cobalt (Co$^{2+}$), iron (Fe$^{2+}$), manganese (Mn$^{2+}$), zinc (Zn$^{2+}$) and copper (Cu$^{2+}$).

With regard to the organic amine salts, mention may be made of primary, secondary or tertiary amine or alkanolamine salts.

The above-mentioned amines contain one or more radicals, which may be identical or different, of linear or branched C$_1$ to C$_{20}$ alkyl type, optionally comprising a hetero atom such as oxygen.

With regard to the quaternary ammonium salts, these comprise three radicals, which may be identical or different, chosen from hydrogen and a linear or branched C$_1$ to C$_{20}$ alkyl radical, optionally comprising a hetero atom such as oxygen.

As mentioned before, when R represents a CH$_2$OH group, then the compound(s) of formula (I) is not gluconic acid (C$_6$H$_{12}$O$_7$), and its salts.

More preferably, the compound(s) of formula (I), when R is a CH$_2$OH group (are), is preferably chosen from mannonic acid, altronic acid, idonic acid, galactonic acid, talonic acid, gulonic acid, allonic acid, a alkali salt thereof, an alkaline-earth metal salt thereof, a transition metal salt thereof, an organic amine salt thereof, and an ammonium salt thereof or a mixture thereof.

In a preferred embodiment of the present invention, R is not a CH$_2$OH group.

When R represents a CO$_2$X group, then the compound(s) of formula (I) is(are) preferably chosen from the group consisting of mucic acid (C$_6$H$_{10}$O$_8$)— also known as galactaric acid,—glucaric acid (C$_6$H$_{10}$O$_8$) and mannaric acid (C$_6$H$_{10}$O$_8$), altaric acid, idaric acid, talaric acid, gularic acid, allaric acid, the alkali metal salts thereof, the alkaline-earth metal salts thereof, the transition metal salts thereof and mixtures thereof, for instance mixtures of mucic acid and of sodium mucate (C$_6$H$_8$O$_8$Na$_2$).

More preferably, the compound(s) of formula (I) is (are) chosen from gluconic acid and mucic acid and its isomers. According to one preferred embodiment of the invention, the compound of formula (I) is mucic acid.

The content of compound of formula (I) is more preferably between 0.001% and 10% by weight relative to the total weight of the composition and preferably between 0.001% and 5% by weight relative to the same reference. The percentages are expressed according to the acid form of the compound of formula (I).

Medium

The medium of the composition that is suitable for dyeing is more preferably an aqueous medium, i.e. a medium comprising water and optionally one or more cosmetically acceptable organic solvents.

By way of example, the said solvents may be chosen preferably from linear or branched, preferably saturated, monoalcohols or diols containing from 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl ether, monoethyl ether and monobutyl ether, propylene glycol or its ethers, for instance propylene glycol monomethyl ether, butylene glycol and dipropylene glycol; and also diethylene glycol alkyl ethers, especially of C1-C4, for instance diethylene glycol monoethyl ether or monobutyl ether, alone or as a mixture.

When they are present in the composition according to the invention, the organic solvent(s) generally represent(s) from 0.5% to 20% by weight relative to the total weight of this composition and preferably from 2% to 10% by weight relative to the same reference.

The composition may also comprise additives that are standard in the field.

Conditioning Polymers

The composition according to the invention may especially comprise at least one cationic or amphoteric conditioning polymer, or mixtures thereof.

It is recalled that, for the purposes of the present invention, the term "cationic conditioning polymer" denotes any polymer containing cationic groups and/or groups that can be ionized into cationic groups, and which makes it possible to improve the cosmetic properties of keratinous fibers, for example, the disentangling, softness, sheen or volume.

The suitable cationic or amphoteric polymers are preferably chosen from those already known in the art per se as improving the cosmetic properties of the hair, for example, those described in the patents and patent applications EP 337

354, FR 2 270 846, FR 2 383 660, FR 2 598 611, FR 2 470 596, FR 2 519 863, FR 2 788 974 and FR 2 788 976 for a list of these compounds.

However, more specific examples of cationic polymers that may be mentioned include cationic polymers comprising at least one primary, secondary, tertiary or quaternary amine group, which may either form a part of the main polymer chain or may be borne by a side substituent directly attached thereto.

More specific examples of these polymers that may be mentioned include:

(1) copolymers of acrylamide and of dimethylaminoethyl methacrylate quaternized with dimethyl sulphate or with a dimethyl halide (Hercofloc from Hercules); copolymers of acrylamide and of methacryloyloxyethyltrimethyl-ammonium chloride (Bina Quat P 100 from Ciba Geigy); the copolymer of acrylamide and of methacryloyloxy-ethyl-trimethylammonium methosulphate (Reten from Hercules); dialkylaminoalkyl acrylate or methacrylate copolymers (Gafquat range from ISP; Copolymer 845, 958 and 937 from ISP); dimethylaminoethyl methacrylate/vinylcaprolactam/vinylpyrroli one terpolymers (Gaffix VC 713 from ISP); vinylpyrrolidone/methacrylamidopropyldimethylamine copolymers (Styleze CC 10 from ISP); vinylpyrrolidone/dimethylaminopropylmethacrylamide quaternized copolymers (Gafquat HS 100 from ISP).

(2) Cellulose ether derivatives comprising quaternary ammonium groups, as described in FR 1 492 597. These polymers are also defined in the CTFA dictionary as quaternary ammoniums of hydroxyethylcellulose which has reacted with an epoxide substituted with a trimethylammonium group.

(3) Cationic cellulose derivatives such as copolymers of cellulose or cellulose derivatives grafted with a water-soluble quaternary ammonium monomer, described in U.S. Pat. No. 4,131,576, such as hydroxyalkyl-celluloses, for instance hydroxymethylcellulose, hydroxyethylcellulose or hydroxypropylcellulose grafted especially with a methacryloylethyltrimethylammonium, methacrylamidopropyltrimethylammonium or dimethyl-diallylammonium salt.

(4) The cationic polysaccharides described in U.S. Pat. Nos. 3,589,578 and 4,031,307, such as guar gums containing trialkylammonium cationic groups. Guar gums modified with a salt, for instance the chloride, preferably 2,3-epoxypropyltrimethylammonium chloride, are used for example.

(5) Polymers consisting of piperazinyl units and of divalent alkylene or hydroxyalkylene radicals containing straight or branched chains, optionally interrupted with oxygen, sulphur or nitrogen atoms or with aromatic or heterocyclic groups, and also the oxidation and/or quaternization products of these polymers. Such polymers are described in FR 2 162 025 and FR 2 280 361.

(6) Water-soluble polyaminoamides prepared preferably by polycondensation of an acidic compound with a polyamine, which are optionally crosslinked, optionally alkylated, or, if they comprise one or more tertiary amine functions, quaternized. These polymers are described in FR 2 252 840 and FR 2 368 508.

(7) Polyaminoamide derivatives resulting from the condensation of polyalkylene polyamines with polycarboxylic acids followed by an alkylation with difunctional agents. Examples that may be mentioned include adipic acid-dialkylaminohydroxyalkyldialkylenetriamine polymers in which the alkyl radical is $C_1$-$C_4$. Such polymers are described in FR 1 583 363.

(8) Polymers obtained by reacting a polyalkylene polyamine comprising two primary amine groups and at least one secondary amine group with a dicarboxylic acid chosen from diglycolic acid and saturated $C_3$-$C_8$ aliphatic dicarboxylic acids, and then with epichlorohydrin. Such polymers are described in U.S. Pat. Nos. 3,227,615 and 2,961,347

(9) Cyclopolymers of alkyldiallylamine or of dialkyldiallylammonium, in homopolymer or copolymer form, as described in FR 2 080 759 and in its Certificate of Addition No. 2 190 406.

(10) Diquaternary ammonium polymers as described in FR 2 320 330, FR 2 270 846, FR 2 316 271, FR 2 336 434, FR 2 413 907, and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,653; 4,026,945; and 4,027,020.

Use may be made of polymers consisting of repeating units corresponding to the following formula:

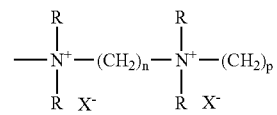

in which the radicals R, which may be identical or different, denote a C1-C4 alkyl or hydroxyalkyl radical, n and p are integers ranging from 2 to 20 and X⁻ is an anion derived from a mineral or organic acid.

(11) Poly(quaternary ammonium) polymers consisting of repeating units of formula:

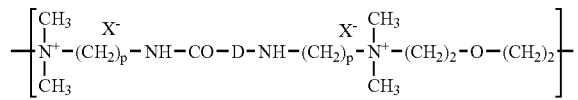

in which p denotes an integer ranging from 1 to 6 approximately, D may be nothing or may represent a group —$(CH_2)_r$—CO— in which r denotes a number equal to 4 or 7, and X⁻is an anion. Such polymers may be prepared according to the processes described in U.S. Pat. Nos. 4,157,388; 4,702,906; 4,719,282; and EP 122 324.

(12) Quaternary polymers of vinylpyrrolidone and of vinylimidazole.

(13) Polyamines of the polyethylene glycol (15) tallow polyamine type (CTFA dictionary name).

(14) Crosslinked methacryloyloxy($C_1$-$C_4$)alkyltri-($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, preferably methylenebis-acrylamide. A crosslinked acrylamide/methacryloyloxyethyl-trimethyl-ammonium chloride copolymer (20/80 by weight) in the form of a dispersion containing 50% by weight of the copolymer in mineral oil (Salcare® SC 92 from Ciba) can be used preferably. A crosslinked methacryloyloxyethyltrimethylammonium chloride homopolymer containing about 50% by weight of the homopolymer in mineral oil or in a liquid ester (Salcare® SC 95, SC 96 from Ciba) can also be used.

Other cationic polymers that can be used in the context of the invention are polyalkyleneimines, preferably polyethyleneimines, polymers containing vinylpyridine or vinylpyridinium units, condensates of polyamines and of epichlorohydrin, quaternary polyureylenes and chitin derivatives.

With regard to the amphoteric polymers, it is possible to use polymers comprising units K and M randomly distributed in the polymer chain, in which K denotes a unit derived from a monomer comprising at least one basic nitrogen atom and M denotes a unit derived from an acidic monomer comprising one or more carboxylic or sulphonic groups, or alternatively K and M may denote groups derived from zwitterionic carboxybetaine or sulphobetaine monomers.

K and M may also denote a cationic polymer chain comprising primary, secondary, tertiary or quaternary amine groups, in which at least one of the amine groups bears a carboxylic or sulphonic group linked via a hydrocarbon-based radical, or alternatively K and M form part of a chain of a polymer containing an α,β-dicarboxylic ethylene unit in which one of the carboxylic groups has reacted with a polyamine comprising one or more primary or secondary amine groups.

The amphoteric polymers corresponding to the above definition that are more particularly preferred are chosen from the following polymers:

(1) Polymers resulting from the copolymerization of a monomer derived from a vinyl compound bearing a carboxylic group such as, preferably, acrylic acid, methacrylic acid, maleic acid, α-chloroacrylic acid, or else a dialkyldiallylammonium salt such as dimethyldiallylammonium chloride, and a basic monomer derived from a substituted vinyl compound containing at least one basic atom, such as, more preferably, dialkylaminoalkyl methacrylate and acrylate, dialkylaminoalkylmethacrylamide and -acrylamide, as described in U.S. Pat. No. 3,836,537. Mention may also be made of the sodium acrylate/acrylamidopropyltrimethylammonium chloride copolymer (Polyquart KE 3033 from Cognis) and the acrylic acid/dimethyldiallylammonium chloride copolymer (Merquat 280, 295, Plus 3330, from Nalco).

(2) Polymers containing units derived from a) at least one monomer chosen from acrylamides and methacrylamides substituted on the nitrogen with an alkyl radical, preferably $C_2$-$C_{12}$ (for example ethyl, tert-butyl, tert-octyl, octyl, decyl or dodecyl), b) at least one acidic monomer containing one or more reactive carboxylic groups (for example acrylic acid, methacrylic acid, crotonic acid or itaconic acid, and monoesters of maleic or fumaric acids or anhydrides), and c) at least one basic monomer such as esters containing primary, secondary, tertiary and quaternary amine substituents of acrylic acid, methacrylic acid, fumaric acid or maleic acid, and the product of quaternization of dimethylaminoethyl methacrylate with dimethyl or diethyl sulphate (for example aminoethyl, butylaminoethyl, N,N'-dimethylaminoethyl or N-tert-butylaminoethyl methacrylates).

Octylacrylamide/acrylate/butylaminoethyl methacrylate copolymers (Amphomer or Lovocryl 47 by the company National Starch) are preferably used.

(3) Crosslinked and partially or totally alkylated polyaminoamides, derived from polyaminoamides of general formula —[CO—R—CO-Z]- in which R is a divalent radical derived from a saturated or unsaturated dicarboxylic acid (for example adipic acid, 2,2,4-trimethyladipic acid, 2,4,4-trimethyladipic acid, terephthalic acid or itaconic acid), from an unsaturated monocarboxylic acid (for instance (meth)acrylic acid), from a $C_1$-$C_6$ alkyl ester of the above-mentioned acids or from a radical derived from the addition of one of these acids to a bis-primary or bis-secondary amine, and Z denotes a radical of a bis-primary, mono- or bis-secondary polyalkylene-polyamine. Preferably, Z represents between 60 and 100 mol %, the radical —NH—[(CH$_2$)$_x$—NH]$_p$ with x=2 and p=2 or 3, or x=3 and p=2; this radical is derived from diethylenetriamine, from triethylenetetramine or from dipropylenetriamine; between 0 and 40 mol % the above radical, in which x=2 and p=1 and which is derived from ethylenediamine, or the radical derived from piperazine —N[CH$_2$CH$_2$]$_2$N—; between 0 and 20 mol %, the radical —NH—(CH$_2$)$_6$—NH— derived from hexamethylenediamine. The crosslinking agent for these polymers is a difunctional agent chosen from epihalohydrins, diepoxides, dianhydrides and bis-unsaturated derivatives, and alkylated by the action of acrylic acid, chloroacetic acid or an alkane sultone (for instance propane sultone or butane sultone) or the alkali metal salts thereof.

(4) Polymers comprising at least zwitterionic units, for instance the butyl methacrylate/dimethylcarboxy-methylammonioethyl methacrylate copolymer (Diaformer Z301 from Sandoz).

(5) Polymers derived from chitosan comprising monomer units corresponding to formulae (A), (B) and (C) below:

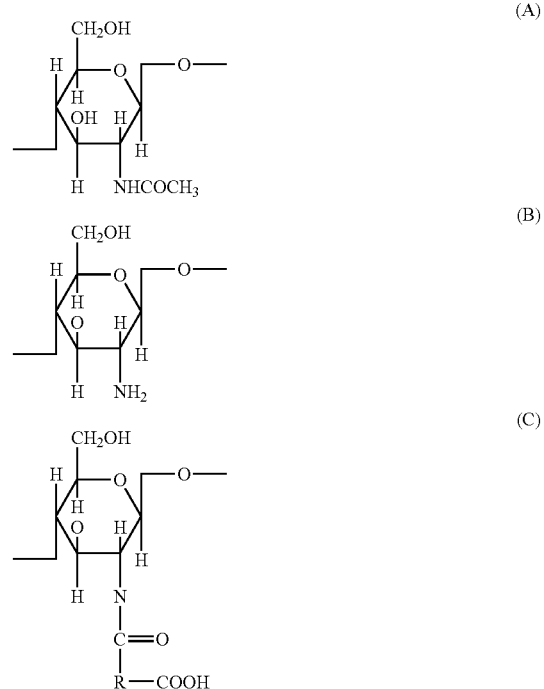

with (A) representing from 0 to 30%, (B) from 5% to 50% and (C) from 30% to 90% in which R represents a radical of formula:

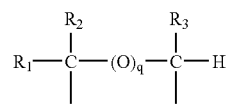

in which q denotes 0 or 1; and if q=0, Ri, which may be identical or different, represent a hydrogen, a methyl, hydroxyl, acetoxy, amino, monoalkylamino or dialkylamino group, optionally interrupted with one or more nitrogen atoms and/or optionally substituted with one or more amine, hydoxyl or carboxyl groups, alkylthio groups optionally bearing an amino group, or sulphonic group; or, if q=1, Ri, which may be identical or different, represent a hydrogen, and also the salts formed by these compounds with acids or bases.

(6) Polymers derived from the N-carboxyalkylation of chitosan, for instance N-carboxymethylchitosan or N-carboxybutylchitosan (Evalsan from Jan Dekker).

(7) Polymers as described in FR 1 400 366:

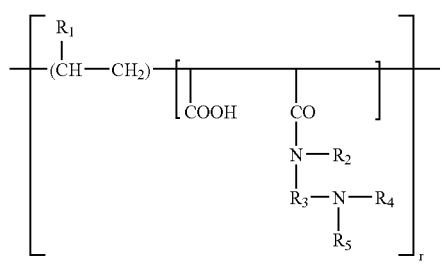

in which $R_1$ is a hydrogen, $CH_3O$—, $CH_3CH_2O$— or phenyl, $R_2$ and $R_5$, which may be identical or different, represent a hydrogen or an alkyl radical (methyl or ethyl), $R_4$ represents an alkyl radical (methyl or ethyl) or a radical of formula —$R_3$—$N(R_5)_2$, $R_3$ representing —$(CH_2)_2$—, —$(CH_2)_3$— or —$CH_2$—$H(CH_3)$— and also the higher homologues of these radicals and containing up to 6 carbon atoms, and r is such that the molecular weight is between 500 and 6 000 000 and preferably between 1 000 and 1 000 000.

(8) Amphoteric polymers of the type -D-X-D-X- chosen from:

a) polymers obtained by the action of chloroacetic acid or sodium chloroacetate on compounds comprising at least one unit of formula -D-X-D-X-D- in which D denotes an —$N[CH_2CH_2]_2N$— (piperazinyl) radical and X denotes the symbol E or E', E or E', which may be identical or different, denote a divalent radical which is an alkylene radical containing a straight or branched chain containing up to 7 carbon atoms in the main chain, optionally substituted with hydroxyl groups and possibly also comprising oxygen, nitrogen or sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;

b) polymers of formula -D-X-D-X- in which D denotes an —$N[CH_2CH_2]_2N$-(piperazinyl) radical and X denotes the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

Among all the cationic or amphoteric polymers that may be used according to the present invention, the following are preferred:

(i) among the cationic polymers:
the dimethyldiallylammonium chloride homopolymer (Merquat 100 from Nalco);
copolymers of dimethyldiallylammonium chloride and of acrylamide (Merquat 2200 from Nalco);
polymers of poly(quaternary ammonium) type prepared and described in FR 2 270 846, consisting of repeating units of formulae (W) and (U) below:

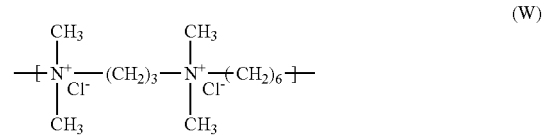

and preferably those with a molecular weight, determined by gel permeation chromatography, of between 9 500 and 9 900;

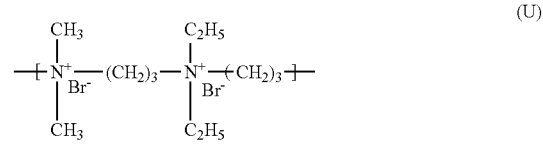

and preferably those with a molecular weight, determined by gel permeation chromatography, of about 1 200;
polymers of poly(quaternary ammonium) type of the family (11) with $X^-$ denoting chlorine, and especially those with a weight-average molecular mass of less than 100 000 and preferably less than or equal to 50 000;

(ii) among the amphoteric polymers:
dimethyldiallylammonium chloride/acrylic acid copolymer (80/20) (Merquat 280 from Nalco—CTFA name: Polyquaternium 22);
dimethyldiallylammonium chloride/acrylic acid copolymer (95/5) (Merquat 295 from Nalco);
methacrylamidopropyltrimonium chloride, acrylic acid and ethyl acrylate copolymer (Merquat 2001 from Nalco—CTFA name: Polyquaternium 47);
acrylamide/dimethyldiallylammonium chloride/acrylic acid terpolymer (Merquat Plus 3330 from Nalco—CTFA name: Polyquaternium 39).

When they are present in the composition, the content of conditioning polymer is between 0.01% and 10% by weight relative to the total weight of the composition and preferably between 0.05% and 5% by weight relative to the same reference.

Amphiphilic polymers containing a hydrophobic chain.

Thus, according to one preferred embodiment of the invention, the composition may comprise at least one amphiphilic polymer comprising at least one hydrophobic chain.

Preferably, when they are present, these amphiphilic polymers are of nonionic, anionic, cationic or amphoteric type. They are preferably of nonionic, anionic or cationic nature.

Preferably, the amphiphilic polymers comprise, as hydrophobic chain, a saturated or unsaturated, aromatic or non-aromatic, linear or branched $C_6$-$C_{30}$ hydrocarbon-based chain, optionally comprising one or more oxyalkylene (oxyethylene and/or oxypropylene) units.

Among the cationic amphiphilic polymers comprising a hydrophobic chain that may be found are cationic polyurethanes or cationic copolymers comprising vinyllactam units and preferably vinylpyrrolidone units.

Even more preferably, the amphiphilic polymers comprising a hydrophobic chain will be of nonionic or anionic nature.

As examples of nonionic amphiphilic polymers containing a hydrophobic chain, mention may be made, inter alia, of:

(1) celluloses modified with groups comprising at least one saturated or unsaturated, linear or branched $C_6$-$C_{30}$ hydrocarbon-based chain, for instance hydroxyethylcelluloses modified with groups comprising at least one hydrophobic chain as defined previously, such as Natrosol Plus Grade 330 CS ($C_{16}$ alkyl—sold by the company Aqualon); Bermocoll EHM 100 (sold by the company Berol Nobel), Amercell Polymer HM-1500 (hydroxyethylcellulose modified with a polyethylene glycol (15) nonylphenyl ether group—sold by the company Amerchol).

(2) hydroxypropylguars modified with groups comprising at least one hydrophobic chain as defined, for example Jaguar XC-95/3 ($C_{14}$ alkyl chain—sold by the company Rhodia Chimie); Esaflor HM 22 ($C_{22}$ alkyl chain—sold by the company Lamberti); RE210-18 ($C_{14}$ alkyl chain) and RE205-1 ($C_{20}$ alkyl chain) sold by the company Rhodia Chimie.

(3) copolymers of vinylpyrrolidone and of hydrophobic monomers containing a hydrophobic chain as defined above, for instance Antaron or Ganex V216 (vinylpyrrolidone/hexadecene copolymers); Antaron or Ganex V220 (vinylpyrrolidone/eicosene copolymers), sold by the company I.S.P.

(4) copolymers of $C_1$-$C_6$ alkyl(meth)acrylates and of amphiphilic monomers containing a hydrophobic chain.

(5) copolymers of hydrophilic (meth)acrylates and of hydrophobic monomers comprising at least one hydrophobic chain, for instance the polyethylene glycol methacrylate/lauryl methacrylate copolymer.

(6) polymers with an aminoplast ether skeleton containing at least one fatty chain, such as the Pure Thix compounds sold by the company Süd-Chemie.

(7) linear (block structure), grafted or starburst polyurethanepolyethers comprising in their chain at least one hydrophilic block, which is generally a polyoxyethylene block which may comprise between 50 and 1 000 oxyethylene units approximately, and at least one hydrophobic block, which may comprise aliphatic groups alone, optionally combined with cycloaliphatic and/or aromatic sequences. Preferably, the polyurethanepolyethers comprise at least two $C_6$-$C_{30}$ hydrocarbon-based hydrophobic chains, separated by a hydrophilic block; the hydrophobic chains may be pendent chains or chains with one or more of the end groups of the hydrophilic block(s).

The polyurethanepolyethers comprise a urethane bond between the hydrophilic blocks, whence the name. By extension, polyurethanepolyethers in which the hydrophilic blocks are linked to the lipophilic blocks via other chemical bonds are also included.

The polyurethanepolyethers that may be used according to the invention are, for example, those described in the article by G. Formum, J. Bakke and Fk. Hansen—Colloid Polym. Sci. 271, 380.389 (1993). Examples of polyurethanepolyethers that may be mentioned include Nuvis FX 1100 (European and U.S. INCI name "Steareth-100/PEG-136/HMDI Copolymer" sold by the company Servo Delden); Rheolate 205, 208, 204 or 212 (sold by the company Rheox); Elfacos T210 ($C_{12}$-$C_{14}$ alkyl chain) and Elfacos T212 ($C_{18}$ alkyl chain) sold by the company Akzo.

The anionic amphiphilic polymers containing a hydrophobic chain that may be used comprise, as hydrophobic chain, at least one saturated or unsaturated, aromatic or non-aromatic, linear or branched $C_8$-$C_{30}$ hydrocarbon-based chain.

More preferably, the anionic amphiphilic polymers comprising at least one hydrophobic chain that may be used in the context of the present invention, which are crosslinked or non-crosslinked, comprise at least one hydrophilic unit derived from one or more ethylenically unsaturated monomers bearing a carboxylic acid function, or a sulphonic function which is free or partially or totally neutralized, and at least one hydrophobic unit derived from one or more ethylenically unsaturated monomers bearing a hydrophobic side chain, and optionally at least one crosslinking unit derived from one or more polyunsaturated monomers.

As ethylenically unsaturated monomers bearing a carboxylic acid function, mention may be made of ethacrylic acid, methacrylic acid and acrylic acid, or mixtures thereof; the last two monomers being preferred.

As examples of ethylenically unsaturated monomers bearing a hydrophobic side chain, mention may be made of esters of unsaturated carboxylic acids such as ethacrylic acid, methacrylic acid or acrylic acid, and of saturated, linear or branched, $C_8$-$C_{30}$ and more preferably $C_{12}$-$C_{22}$ alcohols which are optionally oxyalkylenated (preferably oxyethylenated). They may also be allylic ethers of saturated or unsaturated, aromatic or non-aromatic, branched or unbranched $C_6$-$C_{30}$ alcohols, which are optionally oxyalkylenated (preferably oxyethylenated), more preferably of formula $CH_2=CR'CH_2OB_nR$ with R' representing H or $CH_3$, B representing an ethylenoxy radical, n is an integer between 0 and 100, R represents a hydrocarbon-based radical chosen from alkyl, arylalkyl, aryl, alkylaryl and cycloalkyl radicals containing from 8 to 30 carbon atoms. A unit that is more particularly preferred is such that R' represents hydrogen, n is equal to 10 and R represents a stearyl($C_{18}$) radical.

With regard to the crosslinking monomer, this monomer comprises at least two polymerizable double bonds that are not conjugated with each other. Examples that may be mentioned include diallyl phthalate, allyl(meth)acrylate, divinylbenzene, (poly)ethylene glycol dimethacrylate, methylenebisacrylamide, polyallylsucrose and polyallylpentaerythritol.

Anionic amphiphilic polymers of the type described above are described and prepared, for example, in patents U.S. Pat. Nos. 3,915,921 and 4,509,949 (copolymers of (meth)acrylic acid and of $C_{10}$-$C_{30}$ alkyl(meth)acrylates) or in patent EP 216 479 (copolymers of (meth)acrylic acid and of fatty alkyl allyl ethers).

The amphiphilic polymers comprising at least one sulphonic group, in free or partially or totally neutralized form and at least one hydrophobic portion are described, for example, in FR 00/16954 and FR 01/00328, the content of which forms an integral part of the present invention.

Among these, mention may be made more preferably of acrylamido-2-methyl-2-propanesulphonic (AMPS) acid/n-dodecylacrylamide copolymer neutralized with sodium hydroxide, the copolymer crosslinked with methylenebisacrylamide consisting of 75% by weight of AMPS units neutralized by $NH_3$ and 25% by weight of Genapol T-250 acrylate units, the copolymer crosslinked with allyl methacrylate consisting of 90% by weight of AMPS units neutralized with $NH_3$ and 10% by weight of Genapol T-250 methacrylate units, or the copolymer crosslinked with allyl methacrylate consisting of 80% by weight of AMPS units neutralized with $NH_3$ and 20% by weight of Genapol T-250 methacrylate units.

Examples of preferred polymers that may be mentioned include Carbopol ETD-2020 (acrylic acid/$C_{10}$-$C_{30}$ alkyl methacrylate crosslinked copolymer—sold by the company Noveon); Carbopol 1382, Pemulen TR1 and Pemulen TR2 (acrylic acid/$C_{10}$-$C_{30}$ alkyl acrylate crosslinked copolymers—sold by the company Noveon), the methacrylic acid/ethyl acrylate/oxyethylenated stearyl methacrylate copolymer (55/35/10); the (meth)acrylic acid/ethyl acrylate/25 EO oxyethylated behenyl methacrylate copolymer (Aculyn 28 sold by Rohm & Haas) and the methacrylic acid/ethyl acrylate/steareth-10 allyl ether crosslinked copolymer.

If these amphiphilic polymers are present, their content represents from 0.005% to 20% by weight relative to the total weight of the composition according to the invention, and preferably from 0.1% to 10% by weight relative to the same reference.

Thickeners

The composition may also comprise, as thickener, at least one water-soluble thickening polymer not containing a hydrophobic chain.

The suitable polymers may be of natural origin, or may be synthetic polymers, and are preferably chosen from those conventionally used in cosmetics. In addition, these polymers do not contain a hydrophobic chain, i.e. a saturated or unsaturated, aromatic or non-aromatic, linear or branched $C_8$-$C_{30}$ hydrocarbon-based chain, optionally comprising one or more oxyalkylene (oxyethylene and/or oxypropylene) units. The water-soluble thickening polymers are thus different from the amphiphilic polymers that have just been described.

Examples of synthetic polymers that may be mentioned include polyvinylpyrrolidone, polyacrylic acid, polyacrylamide, non-crosslinked poly(2-acrylamido-propanesulphonic acid) (Simugel EG from the company SEPPIC), crosslinked poly(2-acrylamido-2-methylpropanesulphonic acid), free or partially neutralized with ammonia (Hostacerin AMPS from Clariant), mixtures of non-crosslinked poly(2-acrylamido-2-methylpropanesulphonic acid) with hydroxyalkylcellulose ethers or with poly(ethylene oxide)s, as described in U.S. Pat. No. 4,540,510; mixtures of poly((meth)acrylamido($C_1$-$C_4$)alkylsulphonic acid), which is preferably crosslinked, with a crosslinked copolymer of maleic anhydride and of a ($C_1$-$C_5$)alkyl vinyl ether (Hostacerin AMPS/Stabileze QM from the company ISF).

The thickening polymers of natural origin that may be used according to the present invention are preferably polymers comprising at least one sugar unit, for instance non-ionic guar gums, optionally modified with $C_1$-$C_6$ hydroxyalkyl groups; biopolysaccharide gums of microbial origin, such as scleroglucan gum or xanthan gum; gums derived from plant exudates, such as gum arabic, ghatti gum, karaya gum, gum tragacanth, carrageenan gum, agar gum and carob gum; pectins; alginates; starches; hydroxy($C_1$-$C_6$)alkylcelluloses and carboxy($C_1$-$C_6$)alkylcelluloses.

The term "sugar unit" denotes herein a monosaccharide (i.e., monosaccharide or oside or simple sugar) portion, an oligosaccharide portion (short chains formed from a sequence of monosaccharide units, which may be different) or a polysaccharide portion [long chains consisting of monosaccharide units, which may be different, i.e., polyholosides or polyosides]. The saccharide units may also be substituted with alkyl, hydroxyalkyl, alkoxy, acyloxy or carboxyl radicals, the alkyl radicals containing from 1 to 4 carbon atoms.

Examples of nonionic, unmodified guar gums that may be mentioned, inter alia, include Guargel D/15 (Goodrich); Vidogum GH 175 (Unipectine), Meypro-Guar 50 and Jaguar C (Meyhall/Rhodia Chimie); and the modified nonionic guar gums that may be mentioned include Jaguar HP8, HP60, HP120, DC 293 and HP 105 (Meyhall/Rhodia Chimie); Galactasol 4H4FD2 (Aqualon).

The biopolysaccharide gums of microbial or plant origin are well known to those skilled in the art and are described especially in the book by Robert L. Davidson entitled "Handbook of Water soluble gums and resins" published by McGraw Hill Book Company (1980).

Among these gums, mention will be made of scleroglucans such as, especially, Actigum CS from Sanofi Bio Industries; Amigel from Alban Muller International, and also the glyoxal-treated scleroglucans described in FR 2 633 940); xanthan gums, for instance Keltrol, Keltrol T, Keltrol Tf, Keltrol Bt, Keltrol Rd, Keltrol Cg (Nutrasweet Kelco), Rhodicare S and Rhodicare H (Rhodia Chimie); starch derivatives, for instance Primogel (Avebe); hydroxyethylcelluloses such as Cellosize QP3L, QP4400H, QP30000H, HEC30000A and Polymer PCG10 (Amerchol), Natrosol 250HHR, 250MR, 250M, 250HHXR, 250HHX, 250HR, HX (Hercules) and Tylose H1000 (Hoechst); hydroxypropylcelluloses, for instance Klucel EF, H, LHF, MF and G (Aqualon); carboxymethyl-celluloses, for instance Blanose 7M8/SF, refined 7M, 7LF, 7MF, 9M31F, 12M31XP, 12M31P, 9M31XF, 7H, 7M31, 7H3SXF (Aqualon), Aquasorb A500 (Hercules), Ambergum 1221 (Hercules), Cellogen HP810A, HP6HS9 (Montello) and Primellose (Avebe).

The composition may also comprise as thickener, in replacement for or in combination with at least one water-soluble polymer not containing a hydrophobic chain, at least one linear or non-linear, saturated or unsaturated carboxylic acid alkylamide containing from 6 to 30 carbon atoms, and optionally bearing one or more hydroxyl groups.

Moreover, the nitrogen of the amide group may be monosubstituted or disubstituted. It is preferably monosubstituted.

Finally, according to one preferred embodiment, the amide comprises from 1 to 20, preferably 1 to 10 and more preferably 1 to 5, oxyalkylene (oxyethylene and/or oxypropylene) units. Preferably, the amide bears oxyethylene units.

When they are present, the content of thickeners represents from 0.05% to 20% by weight relative to the total weight of the composition and preferably from 0.1% to 10% by weight relative to the same reference.

Surfactants

The anhydrous bleaching composition may also comprise one or more surfactants, chosen from anionic, nonionic, cationic, amphoteric and zwitterionic surfactants, or mixtures thereof.

By way of example of anionic surfactants that can be used, alone or as mixtures, in the context of the present invention, mention may be made of salts (preferably alkali metal salts, more preferably sodium salts, magnesium salts, ammonium salts, amine salts or amino alcohol salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$-$C_{24}$)alkyl sulphosuccinates, ($C_6$-$C_{24}$)alkyl ether sulphosuccinates, ($C_6$-$C_{24}$)alkylamide sulphosuccinates; ($C_6$-$C_{24}$)alkyl sulphoacetates; ($C_6$-$C_{24}$)acyl sarcosinates and ($C_6$-$C_{24}$)acyl glutamates. It is also possible to use ($C_6$-$C_{24}$)alkylpolyglycoside carboxylic esters such as alkylglycoside citrates, alkylglycoside tartrates and alkylglycoside sulphosuccinates, alkylsulpho-succinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts (for example $C_6$-$C_{24}$) such as oleic, ricinoleic and palmitic acid salts, coconut oil acid or hydrogenated coconut oil acid, and particularly preferably sodium, calcium or magnesium salts of stearic acid; acyl lactylates in which the acyl radical contains 8 to 20 carbon atoms. It is also possible to use alkyl D-galactosideuronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and their salts, preferably those containing from 2 to 50 alkylene oxide groups, preferably ethylene oxide groups, and mixtures thereof.

Without wishing to be limited thereto, the nonionic surfactants may be chosen, alone or as a mixture, from polyethoxylated and/or polypropoxylated alkylphenols, alphadiols or alcohols, having a chain containing, for example, 6 to 24 carbon atoms, it being possible for the number of ethylene oxide and/or propylene oxide groups to range preferably from 1 to 50. Mention may also be made of copolymers of ethylene oxide and of propylene oxide, condensates of ethylene oxide and of propylene oxide with fatty alcohols (for example $C_6$-$C_{24}$); polyethoxylated fatty amides (for example $C_6$-$C_{24}$) preferably having from 2 to 30 mol of ethylene oxide, monoglycerolated or polyglycerolated fatty alcohols (for example $C_6$-$C_{24}$) containing on average 1 to 30 glycerol groups and polyglycerolated fatty amides (for example $C_6$-$C_{24}$) containing on average 1 to 5, and preferably 1.5 to 4, glycerol groups; oxyethylenated fatty acid esters (for example $C_6$-$C_{24}$) of sorbitan having, for example, from 2 to 30 mol of ethylene oxide; fatty acid esters (for example $C_6$-$C_{24}$) of sucrose, fatty acid esters (for example $C_6$-$C_{24}$) of polyethylene glycol, alkylpolyglycosides, N-alkylglucamine derivatives, and amine oxides such as ($C_{10}$-$C_{14}$)alkylamine oxides or N-acylaminopropylmorpholine oxides.

By way of illustration, the amphoteric or zwitterionic surfactants may especially be aliphatic secondary or tertiary amine derivatives in which the aliphatic radical is a linear or branched $C_8$-$C_{18}$ chain containing at least one anionic group of the carboxylate, sulphonate, sulphate, phosphate or phosphonate type; ($C_8$-$C_{20}$)alkylbetaines, ($C_8$-$C_{20}$)alkylsulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Also suitable for use are amphocarboxyglycinates and ampho-carboxypropionates, classified in the CTFA dictionary, 5th edition, 1993, under the names Disodium Cocoamphodiacetate, Disodium Lauroamphodiacetate, Disodium Caprylamphodiacetate, Disodium Caproamphodiacetate, Disodium Cocoamphodipropionate, Disodium Lauroamphodipropionate, Disodium Caprylamphodipropionate, Disodium Caproamphodipropionate, Lauroamphodipropionic acid and Cocoamphodipropionic acid. By way of example, mention may be made of Cocoamphodiacetate (Miranol® C2M Concentrate from Rhodia Chimie).

Among the cationic surfactants, mention may be made, purely as a guide, of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

Preferably, when they are present, the surfactants are chosen from anionic and/or nonionic compounds.

When one or more surfactants are present in the composition, their content is between 0.01% and 40% by weight relative to the total weight of the composition, and referably between 0.1% and 30% by weight relative to the same reference.

Other Additives

The composition may furthermore comprise additives of any other type used, such as reducing agents (for instance thioglycolic acid or its salts, thiolactic acid or its salts, cysteine and cysteamine), UV-screening agents, waxes, volatile or non-volatile, cyclic, linear or branched, organomodified (especially with amine groups) or non-organomodified silicones, preserving agents, ceramides, pseudoceramides, plant, mineral or synthetic oils, vitamins or provitamins, for instance panthenol, opacifiers, etc.

The composition may also comprise mineral or organic fillers (for instance fumed silica of hydrophobic nature), binders, lubricants, antifoams, colorants, mattifying agents, fragrances, etc.

pH of the Composition

It should be noted that the pH of the composition according to the invention is preferably between 4 and 11 and more preferably between 8 and 11.

The pH of the composition may be adjusted using a basifying agent or an acidifying agent.

As examples of acidifying agents that may be used, mention may be made of mineral or organic acids, for instance hydrochloric acid, phosphoric acid, orthophosphoric acid, acetic acid, tartaric acid, citric acid, lactic acid, boric acid and sulphonic acids.

The basifying agents may themselves be chosen especially from aqueous ammonia, ammonium or alkaline carbonates, alkanolamines such as monoethanolamine, diethanolamine and triethanolamine and derivatives thereof, hydroxyalkylamines, oxyethylenated and/or oxypropylenated ethylenediamines, sodium hydroxide, potassium hydroxide and the compounds corresponding to the following formula:

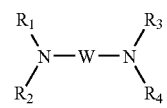

in which W is a propylene residue optionally substituted with a hydroxyl group or a $C_1$-$C_6$ alkyl radical; $R_1$, $R_2$, $R_3$ and $R_4$, which may be identical or different, represent a hydrogen atom or a $C_1$-$C_6$ alkyl radical optionally bearing at least one hydroxyl radical.

Usually, the composition has a content of acidifying or basifying agent, when they are present, of between 0.01% and 30% by weight relative to the total weight of the composition.

The composition according to the invention may be in various forms, such as liquids, creams, gels or pastes, or in any other suitable form.

Another preferred embodiment of the present invention consists of a ready-to-use composition comprising the composition that has just been detailed and at least one oxidizing agent.

In one preferred embodiment of the invention, this ready-to-use composition may be obtained by extemporaneous mixing of a composition as described above and at least one oxidation base and/or at least one direct dye with a composition comprising at least one oxidizing agent.

Preferably, the oxidizing agent is chosen from hydrogen peroxide, urea peroxide, alkali metal bromates, persalts such as perborates, percarbonates and persulphates, peracids, enzymes such as peroxidases and 2-electron or 4-electron oxidoreductases, or mixtures thereof.

The content of oxidizing agent(s) more preferably represents from 0.1% to 30% by weight relative to the weight of the oxidizing composition and preferably from 0.5% to 20% by weight relative to the same reference.

Moreover, in accordance with another preferred embodiment of the invention, the content of oxidizing agent is between 5% and 20% by weight relative to the ready-to-use composition.

The medium of the oxidizing composition is a medium that is suitable for dyeing and may be chosen from those listed in the context of the composition according to the invention. Reference may thus be made thereto.

It should be noted that the pH of the ready-to-use composition is preferably between 4 and 12, more preferably between 7 and 11.5 and preferably between 8 and 11.

Yet another preferred embodiment of the invention is a process for dyeing or keratin fibers, successively comprising the following steps:
a) a mixing composition according to the invention comprising at least one oxidation base or direct dye or a mixture thereof, at least one above-mentioned compound of formula (I), a suitable medium and optionally an oxidizing composition, are applied to the keratin fibers;
b) applying the mixed composition contemporaneously;
c) leaving the composition on the fibers for a time that is sufficient to obtain the desired coloration;
d) rinsing the keratin fibers to remove therefrom the composition according to the invention and optionally the oxidizing composition;
e) optionally washing and rinsing the keratin fibers; and
f) optionally dying the fibers.

It is pointed out that the process according to the invention is preferably suitable for dyeing human keratinous fibers, and preferably the hair, the eyelashes, the eyebrows, the beard and the moustache.

According to a preferred embodiment of the invention, the process is performed with a composition comprising at least one direct dye and at least one compound of formula (I) in the absence of oxidizing composition. It should be noted that, according to this embodiment, the composition according to the invention does not comprise any oxidation base or any coupler.

According to another preferred embodiment of the process, this process is performed with a composition comprising at least one oxidation base, optionally combined with at least one coupler, or direct dye, and at least one compound of formula (I) in the presence of an oxidizing composition.

According to this embodiment, the process may comprise a preliminary step comprising separately storing the composition according to the invention and the oxidizing composition, and then mixing them together at the time of use, followed by applying this mixture to the keratinous fibers for a time that is sufficient to develop the desired coloration, after which the fibers are rinsed, optionally washed with shampoo, rinsed again and optionally dried.

The constituent components and the respective amounts thereof have been defined previously in the description and reference may be made thereto.

Preferably, the oxidizing composition is used in an amount such that the content of oxidizing agent in the mixture comprising the composition according to the invention and the oxidizing composition (ready-to-use composition) is between 5% and 20% by weight relative to the weight of the ready-to-use composition.

Irrespective of the adopted variant of the process, the temperature required to develop the coloration is generally between room temperature (15 to 25° C.) and 80° C. and more preferably between 15 and 40° C.

Usually, the leave-in time ranges between 1 and 60 minutes and more preferably between 10 and 50 minutes.

Lastly, a final preferred embodiment of the invention comprises a device for dyeing keratinous fibers, comprising at least two compartments, wherein one of the at least two compartments comprise a composition according to the invention, the other at least two compartments comprises an oxidizing composition comprising at least one oxidizing agent in a medium that is suitable for dyeing.

Everything that has been mentioned hereinabove regarding the nature and amounts of the various constituent components of the composition according to the invention and of the oxidizing composition remains valid and will not berepeated in this section of the description.

Concrete but non-limiting examples of the invention will now be presented.

EXAMPLE 1

The formulation below, in liquid form, is prepared:

| | |
|---|---|
| Oleyl alcohol | 4% |
| Polyglycerolated (2 mol) oleyl alcohol | 8% |
| [Chimexane NB - sold by Chimex] | |
| Polyglycerolated (4 mol) oleyl alcohol | 5% |
| [Chimexane NC - sold by Chimex] | |
| Diethylaminopropyl laurylaminosuccinamate | 2% |
| at 55% in water | |
| [Chimexane HB - sold by Chimex] | |
| Oleic acid | 5% |
| (C13/C15) alkyl ether carboxylic acid | 12% |
| monoethanolamide (2 EO) | |
| [AminolA15 - sold by Chemy] | |
| Oxyethylenated oleylamine (2 EO) | 5% |
| [Rhodameen 02 - sold by Rhodia Chimie] | |
| Ethanol | 9% |
| Propylene glycol | 5% |
| Butoxydiglycol | 10% |
| Gluconic acid at 50% in water | 1% |
| [Gluconal GA-50-SG - sold by Akzo] | |
| 1,3-Dihydroxybenzene (resorcinol) | 0.085% |
| para-Phenylenediamine | 0.27% |
| 5-N-(β-Hydroxyethyl)amino-2-methylphenol | 0.16% |
| 2-Methyl-5-aminophenol | 1.12% |
| para-Aminophenol | 0.2% |
| 6-Hydroxyindole | 0.045% |

-continued

| | |
|---|---|
| Antioxidant | qs |
| Reducing agent | qs |
| Fragrance | qs |
| Aqueous ammonia (20% NH$_3$) | 10.2% |
| Water | qs 100% |

The percentages are expressed on a weight basis.

At the time of use, this composition is mixed weight-for-weight with an oxidizing composition with a hydrogen peroxide titre of 6%, and the mixture obtained is applied to hair for 30 minutes and then rinsed out.

A relatively unselective shade (reduced coloration difference between the differently sensitized hair or portion of hair) is obtained.

EXAMPLE 2

The formulation below, in liquid form, is prepared:

| | |
|---|---|
| Cetylstearyl alcohol | 13% |
| Oxyethylenated lauryl alcohol (12 EO) | 8% |
| Oxyethylenated decyl alcohol (3 EO) at 55% in water [Empilan KA 2.5/90FL - sold by Huntsman] | 6% |
| Oxyethylenated oleocetyl alcohol (30 EO) | 4% |
| Lauric acid | 5% |
| Monoethanolamine | 2% |
| Propylene glycol | 8% |
| Tetramethylhexamethylenediamine/1,3-dichloropropylene polycondensate at 60% in water [Mexomere PO - sold by Chimex] | 1% |
| Dimethyldiallylammonium chloride/acrylic acid copolymer (80/20) at 40.5% in water [Merquat 280 - sold by Nalco] | 2% |
| Glycol distearate | 4% |
| Fumed silica of hydrophobic nature | 2% |
| Crosslinked polyacrylic acid [Carbopol 980 - sold by Noveon] | 0.6% |
| Mucic acid [Muciliance - sold by Soliance] | 1% |
| 1,3-Dihydroxybenzene (resorcinol) | 0.67% |
| para-Phenylenediamine | 0.88% |
| 5-N-(β-Hydroxyethyl)amino-2-methylphenol | 0.055% |
| 2-Methyl-1,3-dihydroxybenzene | 0.11% |
| para-Aminophenol | 0.27% |
| 4-(Methylamino)phenol hemisulphate | 0.26% |
| 1-Hydroxy-3-aminobenzene | 0.16% |
| Antioxidant | qs |
| Reducing agent | qs |
| Fragrance | qs |
| Aqueous ammonia (20% NH$_3$) | 11.1% |
| Water | qs 100% |

The percentages are expressed on a weight basis.

At the time of use, this composition is mixed with its weight equivalent of an oxidizing composition with a hydrogen peroxide titre of 6%, and the mixture obtained is applied to hair for 30 minutes and then rinsed out.

A relatively unselective shade (reduced coloration difference between the differently sensitized hair or portion of hair) is obtained.

The invention claimed is:

1. A composition for dyeing a keratinous fiber comprising:
   a) at least one oxidation base or direct dye or a mixture thereof;
   b) at least one compound of formula (I):

$$R-(CHOH)_4-CO_2X \qquad (I),$$

wherein
   R represents a CH$_2$OH or CO$_2$X group, and
   X represents a hydrogen atom or a monovalent or divalent cation chosen from an alkali metal, alkaline-earth metal, transition metal, organic amine or ammonium ion, and
   c) a suitable medium,
wherein when R is a CH$_2$OH group, said compound of formula (I) is not gluconic acid or its salt.

2. The composition of claim 1, wherein said keratinous fiber is hair.

3. The composition of claim 1, wherein said compound of formula (I) is mannonic acid, altronic acid, idonic acid, galactonic acid, talonic acid, gulonic acid, allonic acid, or an alkali metal salt thereof, an alkaline-earth metal salt thereof, a transition metal salt thereof, an organic amine salt thereof, an ammonium salt thereof, or a mixture thereof.

4. The composition of claim 1, wherein said R is not a CH$_2$OH group.

5. The composition of claim 1, wherein said compound of formula (I) is mucic acid, glucaric acid, mannaric acid, altaric acid, idaric acid, talaric acid, gularic acid allaric acid, an alkali metal salt thereof, an alkaline-earth metal salt thereof or a transition metal salt thereof, an organic amine salt thereof, an ammonium salt thereof or a mixture thereof.

6. The composition of claim 5, wherein said compound of formula (I) is mucic acid.

7. The composition of claim 1, wherein the content of said compound of formula (I) is from 0.001% to 10% by weight relative to the total weight of the composition.

8. The composition of claim 7, wherein said content of said compound of formula (I) is from 0.001% to 5% by weight relative to the total weight of the composition.

9. The composition of claim 1, wherein said oxidation base is para-phenylenediamine, bis(phenyl)alkylenediamine, para-aminophenol, ortho-aminophenol or heterocyclic base, or a salt thereof with an acid or with an alkaline agent, or a mixture thereof.

10. The composition of claim 1, wherein the content of said oxidation base is from 0.0005% to 12% by weight relative to the total weight of the composition.

11. The composition of claim 10, wherein said content of said oxidation base is from 0.005% to 6% by weight relative to the total weight of the composition.

12. The composition of claim 1, further comprising at least one coupler.

13. The composition of claim 12, wherein said coupler is a meta-phenylenediamine, meta-aminophenol, meta-diphenol or heterocyclic coupler, ora salt thereof with an acid or with an alkaline agent, or a mixture thereof.

14. The composition of claim 12, wherein the content of said coupler is from 0.0001% to 10% by weight relative to the total weight of the composition.

15. The composition of claim 14, wherein said content of said coupler is from 0.005% to 5% by weight relative to the total weight of the composition.

16. The composition of claim 1, wherein said direct dye is a nitrobenzene dye, azo dye, anthraquinone dye, naphthoquinone dye, benzoquinone dye, phenothiazine dye, indigoid dye, xanthene dye, phenanthridine dye, phthalocyanin dye or a dye derived from triarylmethane, or a mixture thereof.

17. The composition of claim 1, wherein the content of said direct dye is from 0.0005% to 12% by weight relative to the total weight of the composition.

18. The composition of claim 17, wherein said content of said direct dye is from 0.005% to 6% by weight relative to the total weight of the composition.

19. The composition of claim 1, wherein said suitable medium is an aqueous medium.

20. The composition of claim 19, wherein said aqueous medium comprises water and optionally at least one cosmetically acceptable organic solvent.

21. The composition of claim 20, wherein said cosmetically acceptable organic solvent is a linear or branched, saturated or unsaturated, monoalcohol or diol containing from 2 to 10 carbon atoms, or an aromatic alcohol, glycol or glycol ether, or a mixture thereof.

22. The composition of claim 21, wherein the content of said cosmetically acceptable organic solvent is from 0.5% to 20% by weight relative to the total weight of the composition.

23. The composition of claim 22, wherein said content of said cosmetically acceptable organic solvent is from 2% to 10% by weight relative to the total weight of the composition.

24. The composition of claim 1, further comprising a conditioning polymer.

25. The composition of claim 24, wherein said conditioning polymer is a cationic or amphoteric conditioning polymer or a mixture thereof.

26. The composition of claim 24, wherein the content of said conditioning polymer is from 0.01% to 10% by weight relative to the total weight of the composition.

27. The composition of claim 26, wherein said content of said conditioning polymer is from 0.05% to 5% by weight relative to the total weight of the composition.

28. The composition of claim 1, further comprising a surfactant.

29. The composition of claim 28, wherein said surfactant is nonionic, anionic, cationic, amphoteric or zwitterionic surfactant, or a mixture thereof.

30. The composition of claim 28, wherein the content of said surfactant is from 0.01% to 40% by weight relative to the total weight of the composition.

31. The composition of claim 30, wherein said content of said surfactant is from 0.1% to 30% by weight relative to the total weight of the composition.

32. The composition of claim 1, further comprising at least one amphiphilic polymer with a hydrophobic chain.

33. The composition of claim 32, wherein said at least one amphiphilic polymer with said hydrophobic chain is nonionic, anionic, cationic or amphoteric polymer with a hydrophobic chain.

34. The composition of claim 32, wherein the content of said amphiphilic polymer with said hydrophobic chain is from 0.005% to 20% by weight relative to the total weight of the composition.

35. The composition of claim 34, wherein said content of said amphiphilic polymer with said hydrophobic chain is from 0.1% to 10% by weight relative to the total weight of the composition.

36. The composition of claim 1, further comprising at least one thickener.

37. The composition of claim 36, wherein said thickner is a water-soluble thickening polymer not containing a hydrophobic chain.

38. The composition of claim 36, wherein the content of said thickener is from 0.05% to 20% by weight relative to the total weight of the composition.

39. The composition of claim 38, wherein said content of said thickener is from 0.1% to 10% by weight relative to the total weight of the composition.

40. The composition of claim 1, further comprising at least one acidifying or basifying agent.

41. The composition of claim 40, wherein the content of said acidifying or basifying agent is from 0.01% to 30% by weight relative to the total weight of the composition.

42. The composition of claim 1, wherein said composition is in the form of liquid, cream, gel, or paste.

43. The composition of claim 1, further comprising at least one material selected from the group consisting of a coupler, conditioning polymer, surfactant, amphiphilic polymer with a hydrophobic chain, thickener, acidifying agent and basifying agent.

44. The composition of claim 43, wherein said coupler is a meta-phenylenediamine, meta-aminophenol, meta-diphenol or heterocylic coupler or a salt thereof with an acid or with an alkaline agent, and is provided in an amount of from 0.0001% to 10% by weight relative to the total weight of the composition.

45. The composition of claim 43, wherein said conditioning polymer is a cationic or amphoteric conditioning polymer or a mixture thereof, and is provided in an amount of from 0.01% to 10% by weight relative to the total weight of the composition.

46. The composition of claim 43, wherein said surfactant is a nonionic, anionic, cationic, amphoteric or zwitterionic surfactant or a mixture thereof, and is provided in an amount of from 0.01% to 40% by weight relative to the total weight of the composition.

47. The composition of claim 43, wherein said amphiphilic polymer with a hydrophobic chain is a nonionic, anionic, cationic or amphoteric polymer with a hydrophobic chain, and is provided in an amount of from 0.005% to 20% by weight relative to the total weight of the composition.

48. The composition of claim 43, wherein said thickener is a water-soluble thickening polymer not containing a hydrophobic chain, and is provided in an amount of from 0.05% to 20% by weight relative to the total weight of the composition.

49. The composition of claim 43, wherein the content of said acidifying agent or said basifying agent is from 0.01% to 30% by weight relative to the total weight of the composition.

50. The composition of claim 1, further comprising at least two materials selected from the group consisting of a coupler, conditioning polymer, surfactant, amphiphilic polymer with a hydrophobic chain, thickener, acidifying agent and basifying agent.

51. The composition as in claim 43 or 50, wherein said composition is in the form of liquid, cream, gel or paste.

52. A ready-to-use composition comprising:
a) said composition as in claim 1, 43 or 50, and
b) at least one oxidizing composition comprising at least one oxidizing agent in a medium suitable for dying.

53. The ready-to-use composition of claim 52, wherein said oxidizing agent is hydrogen peroxide, urea peroxide, alkali metal bromate, persalt, peracids, or enzyme, or a mixture thereof.

54. The ready-to-use composition of claim 53, wherein said persalt is perborate, percarbonate or persulphate.

55. The ready-to-use composition of claim 53, wherein said enzyme is peroxidase, or two electron or four electron oxidoreductase.

56. The ready-to-use composition of claim 52, wherein the content of said oxidizing agent is from 0.1% to 30% by weight relative to the weight of the oxidizing composition.

57. The ready-to-use composition of claim 56, wherein said content of said oxidizing agent is from 0.5% to 20% by weight relative to the total weight of the oxidizing composition.

58. The ready-to-use composition of claim 57, wherein said content of said oxidizing agent from 5% to 20% by weight relative to the oxidizing composition.

59. A process for dyeing a keratinous fiber comprising:
a) mixing said composition as in claim 1, 43 or 50 and optionally an oxidizing composition comprising at least one oxidizing agent in a medium suitable for dyeing;
b) applying said mixed composition to said keratinous fiber shortly after mixing;
c) leaving said mixed composition on said keratinous fiber for sufficient time to obtain a desired coloration;
d) rinsing said keratinous fiber to remove said mixed composition from said keratinous fiber;
e) optionally washing and rinsing said keratinous fiber; and
f) optionally drying said keratinous fiber.

60. The process of claim 59, wherein said keratinous fiber is hair.

61. A device for dyeing a keratinous fiber comprising:
a) at least two compartments, wherein
one of said at least two compartments comprises said composition as in claim 1, 43 or 55, and
another one of at least two compartments comprises an oxidizing composition comprising at least one oxidizing agent in a medium that is suitable for dyeing.

* * * * *